US009993322B2

(12) United States Patent
Kubalak et al.

(10) Patent No.: US 9,993,322 B2
(45) Date of Patent: Jun. 12, 2018

(54) METHOD OF IMPLANTING A URINARY CONTROL SYSTEM THROUGH A SINGLE SKIN INCISION

(71) Applicant: Coloplast A/S, Humlebaek (DK)

(72) Inventors: Thomas Kubalak, Wayzata, MN (US); Christopher Deegan, North St. Paul, MN (US); Daniella Fay Terry, Fridley, MN (US)

(73) Assignee: Coloplast A/S, Humlebaek (DK)

( * ) Notice: Subject to any disclaimer, the term of this patent is extended or adjusted under 35 U.S.C. 154(b) by 256 days.

(21) Appl. No.: 14/722,169

(22) Filed: May 27, 2015

(65) Prior Publication Data
US 2016/0346071 A1    Dec. 1, 2016

(51) Int. Cl.
*A61F 2/04* (2013.01)
*A61F 2/00* (2006.01)

(52) U.S. Cl.
CPC ...... *A61F 2/004* (2013.01); *A61F 2250/0003* (2013.01); *A61F 2250/0013* (2013.01)

(58) Field of Classification Search
CPC .... A61F 2/0004; A61F 2/0013; A61F 2/0027; A61F 2250/0003; A61F 2250/0013; A61F 2/004
See application file for complete search history.

(56) References Cited

U.S. PATENT DOCUMENTS

| 3,744,063 | A | 7/1973 | McWhorter et al. |
| 4,063,548 | A | 12/1977 | Klatt et al. |
| 4,222,377 | A | 9/1980 | Burton |
| 4,412,530 | A | 11/1983 | Burton |
| 4,682,583 | A | 7/1987 | Burton et al. |
| 4,878,889 | A | 11/1989 | Polyak |
| 5,078,720 | A | 1/1992 | Burton et al. |
| 5,335,669 | A | 8/1994 | Tihon et al. |
| 5,518,504 | A | 5/1996 | Polyak |
| 2003/0046111 | A1 | 3/2003 | Snitkin |
| 2003/0100839 | A1 | 5/2003 | Cohen et al. |
| 2003/0100930 | A1 | 5/2003 | Cohen et al. |
| 2008/0004487 | A1 | 1/2008 | Haverfield |
| 2010/0211175 | A1* | 8/2010 | Gomez-Llorens ........ A61F 2/26 623/14.13 |

(Continued)

FOREIGN PATENT DOCUMENTS

DE    8905856 U1    10/1989
DE    9010783 U1    9/1990

(Continued)

OTHER PUBLICATIONS

American Medical Systems, AMS 800TM, Urinary Control System Operating Room, Manual, Mar. 2004.

*Primary Examiner* — Thaddeus Cox
(74) *Attorney, Agent, or Firm* — Coloplast Corp., Coloplast A/S; Nick Baumann

(57) ABSTRACT

A method of treating urinary incontinence includes removing a urinary control system from a package, where the urinary control system has three components including a cuff attachable to a pump and a reservoir attachable to the pump. The method includes forming one skin incision in a patient, and implanting the three components of the urinary control system into the patient through the one skin incision.

7 Claims, 8 Drawing Sheets

(56) References Cited

U.S. PATENT DOCUMENTS

| | | | |
|---|---|---|---|
| 2010/0312052 A1* | 12/2010 | Morningstar | A61F 2/004 600/40 |
| 2013/0079587 A1* | 3/2013 | Crabtree | A61F 2/0031 600/31 |
| 2015/0025303 A1* | 1/2015 | Deitch | A61F 2/004 600/31 |
| 2015/0045609 A1* | 2/2015 | Anderson | A61F 2/004 600/31 |

FOREIGN PATENT DOCUMENTS

| | | |
|---|---|---|
| EP | 0421031 A1 | 4/1991 |
| IE | 913252 A1 | 2/1992 |
| IL | 92229 | 7/1990 |
| WO | 9304727 A1 | 3/1993 |
| WO | 9503848 A1 | 2/1995 |
| WO | 9618431 A1 | 6/1996 |
| WO | 0160283 A2 | 8/2001 |
| WO | 0167996 A2 | 9/2001 |

\* cited by examiner

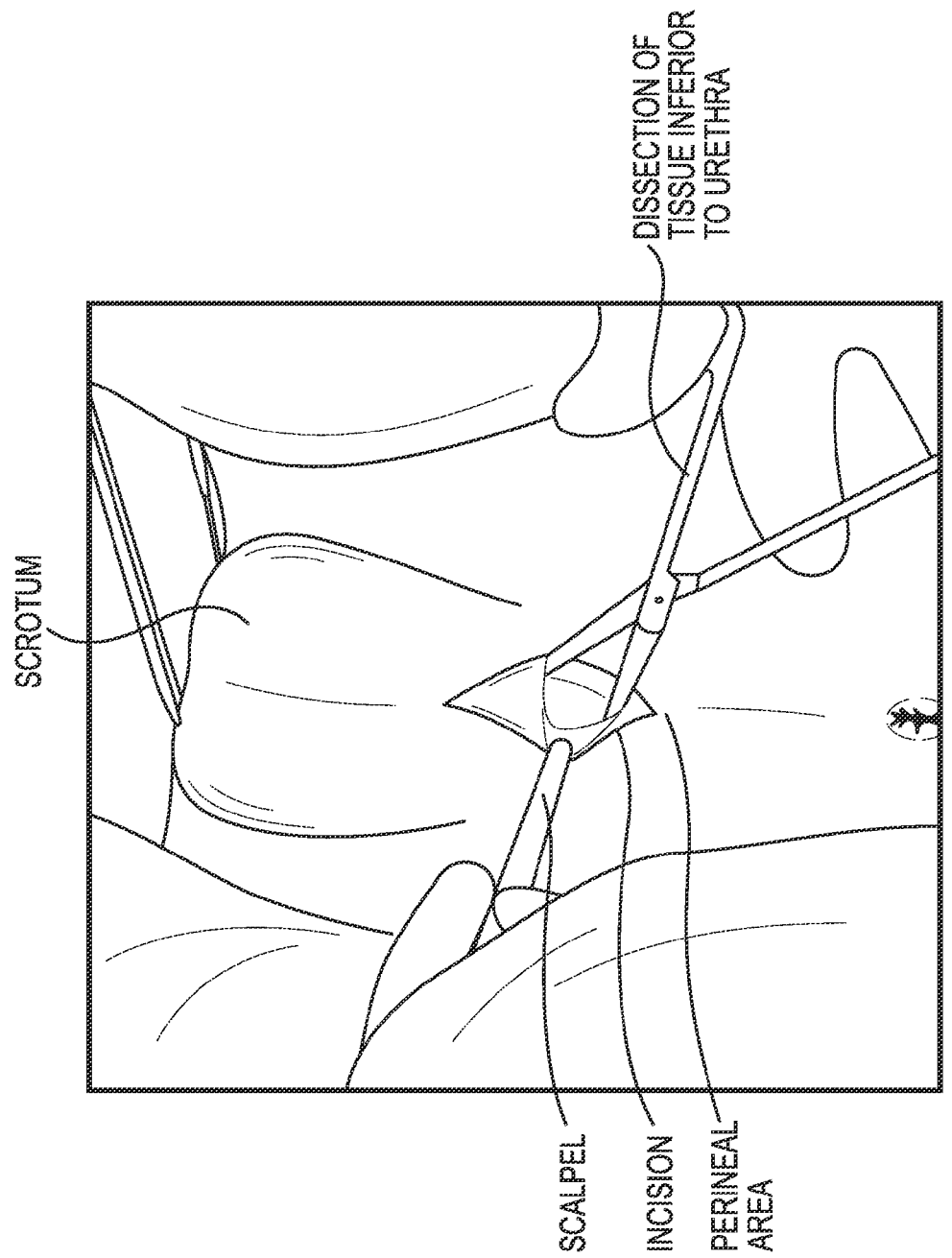

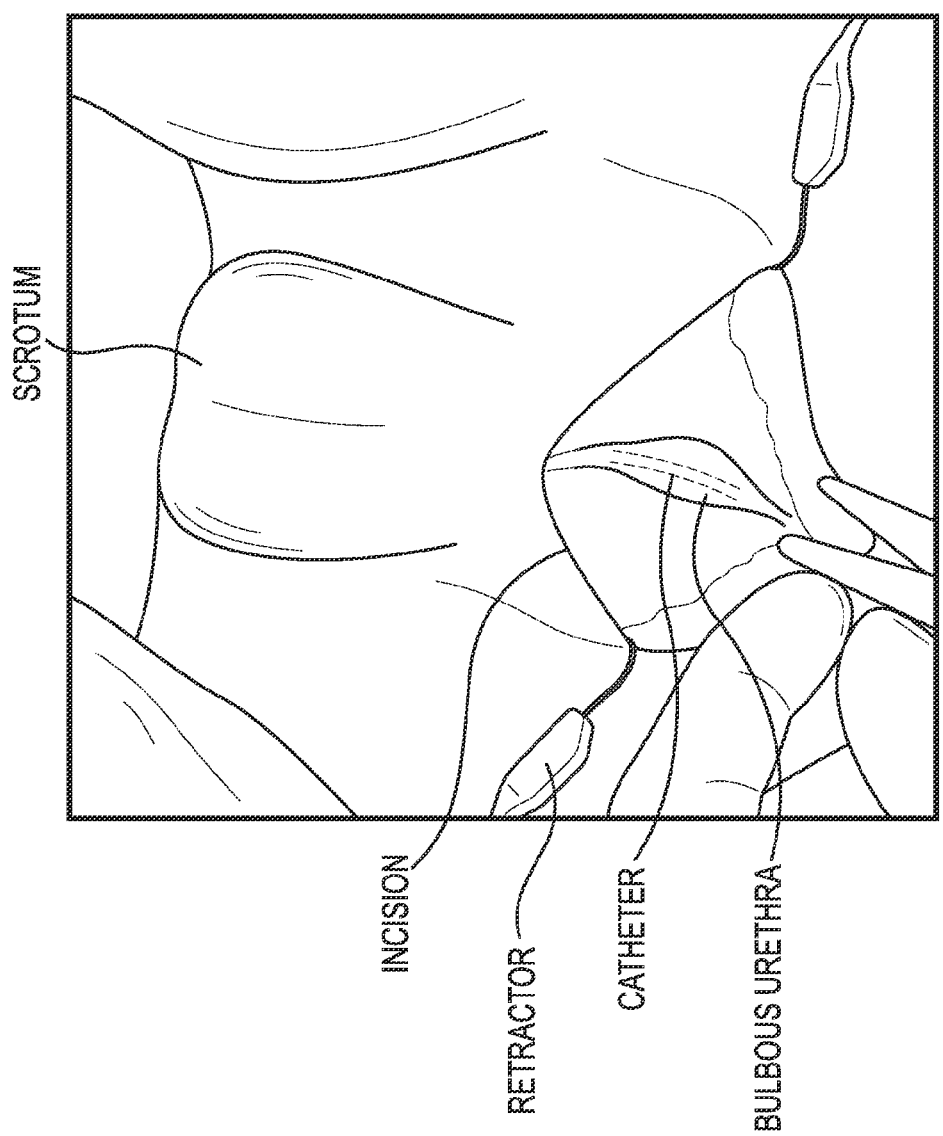

METHOD OF IMPLANTING A URINARY CONTROL SYSTEM THROUGH A SINGLE SKIN INCISION

SUMMARY

A minimally invasive surgical procedure is taught providing the implantation of a urinary control system to treat urinary incontinence through a single (one and only one) skin incision in the patient.

One aspect provides a method of implanting a urinary control system in a patient. The method includes:
forming one and only one incision in skin of the patient;
dissecting pelvic floor muscle through the one and only one incision and exposing a bulbous urethra of the patient;
passing a cuff of the urinary control system through the one and only one incision and through the pelvic floor muscle and securing the cuff around the bulbous urethra of the patient;
passing a reservoir of the urinary control system through the one and only one incision and through the pelvic floor muscle and placing the reservoir superior relative to a pubic bone of the patient;
inserting a pump of the urinary control system through the one and only one incision and into a scrotum of the patient; and
connecting the cuff to the pump and connecting the reservoir to the pump.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3 is a schematic view of a surgical procedure forming a single skin incision in a male patient.

FIG. 4 is a schematic view of tissue dissected to expose a bulbous urethra of the male patient.

DETAILED DESCRIPTION

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments described in this application, may be combined with each other ("mixed and matched"), unless specifically noted otherwise.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

The removal of the prostate gland in men can result in a reduced efficiency of the urinary sphincter, which can result in urinary incontinence. In some instances, the removal of the prostate gland also results in the removal, or partial removal, of the urinary sphincter. One solution is to place an artificial sphincter around the urethra. One artificial sphincter includes a cuff implanted through a first incision and placed around the urethra. The cuff is attached to a pump that is usually placed in the scrotum. The pump moves liquid from the cuff to a reservoir to deflate the cuff and allow the user to pass urine. The liquid is allowed to move from the reservoir back to the cuff to coapt or close the urethra, which provides the user with continence. The reservoir is placed in the abdomen through a separate, second skin incision.

Surgeons have voiced a preference for minimally invasive surgical procedures that are realized through fewer incisions and are associated with less time in the surgical suite, all of which reduces the cost of the surgery.

Embodiments provide a method of implantation of a cuff, a pump, and a reservoir of a urinary control system all through one and only one skin incision.

Figure 1:
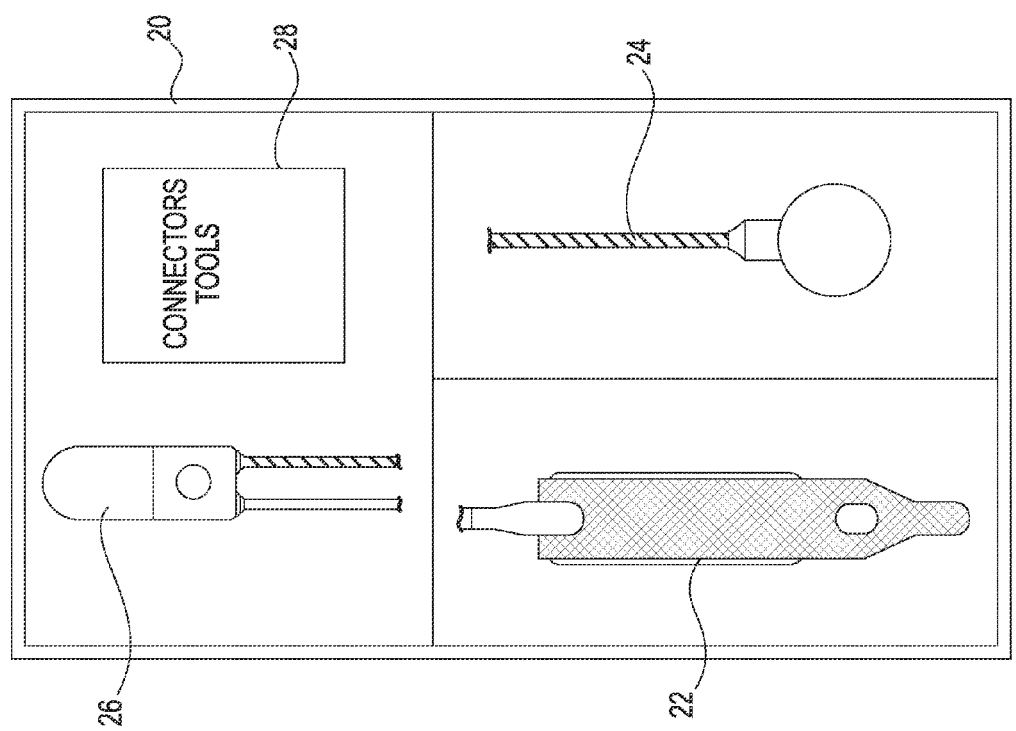
FIG. 1 is a top view of one embodiment of a kit containing a packaged urinary control system.

FIG. 1 is a top view of a package 20 containing a kit of parts of a urinary control system. The urinary control system includes a cuff 22 that is sized for implantation around the urethra, a pressure regulating balloon 24 that is implantable in a retropubic space, and a pump 26 to move liquid between the pressure regulating balloon 24 and the cuff 22. The pressure regulating balloon 24 is a reservoir that holds liquid for the system at a certain elevated pressure, and the pressure in the liquid is useful in maintaining the cuff 22 in a closed state. The user operates the pump 26 to move liquid out of the cuff 22 and into the reservoir 24 to open the cuff 22, which allows the user to void urine. After the user has passed urine, the pressurized liquid in the reservoir 24 flows back into the cuff 22 to close the urethra. The package 20 is sized to contain at least the three components of the urinary control system and other ancillary items such as connectors/tools 28 that are useful when connecting parts of the urinary control system.

Figure 2:
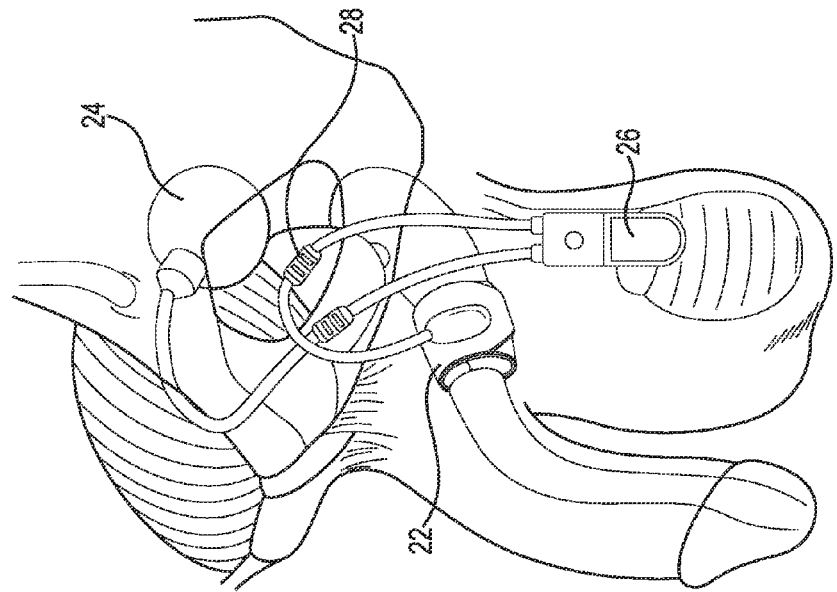
FIG. 2 is a schematic view of components of the urinary control system of FIG. 1 implanted in a male patient.

FIG. 2 is a schematic view of the urinary control system described in FIG. 1 implanted in a male patient. The cuff 22 is attached around the bulbous urethra. The pressure regulating balloon 24 is placed in the retropubic space. The pump 26 is placed in the scrotum. Connectors 28 are used to attach the cuff 22 to the pump 26 and to connect the reservoir 24 to the pump 26.

Embodiments provide a method of implanting urinary control system in a patient through one and only one incision formed in the skin of the patient.

Other approaches to implanting the urinary control system include forming a first incision to access the urethra and a second incision through the abdomen to place the pressure regulating balloon in a retropubic space.

In contrast, embodiments of the approach described below implants all three components of the urinary control system through one and only one incision formed in the skin. This new approach is less invasive and requires fewer incisions, thus allowing the patient to heal faster.

Figure 5:
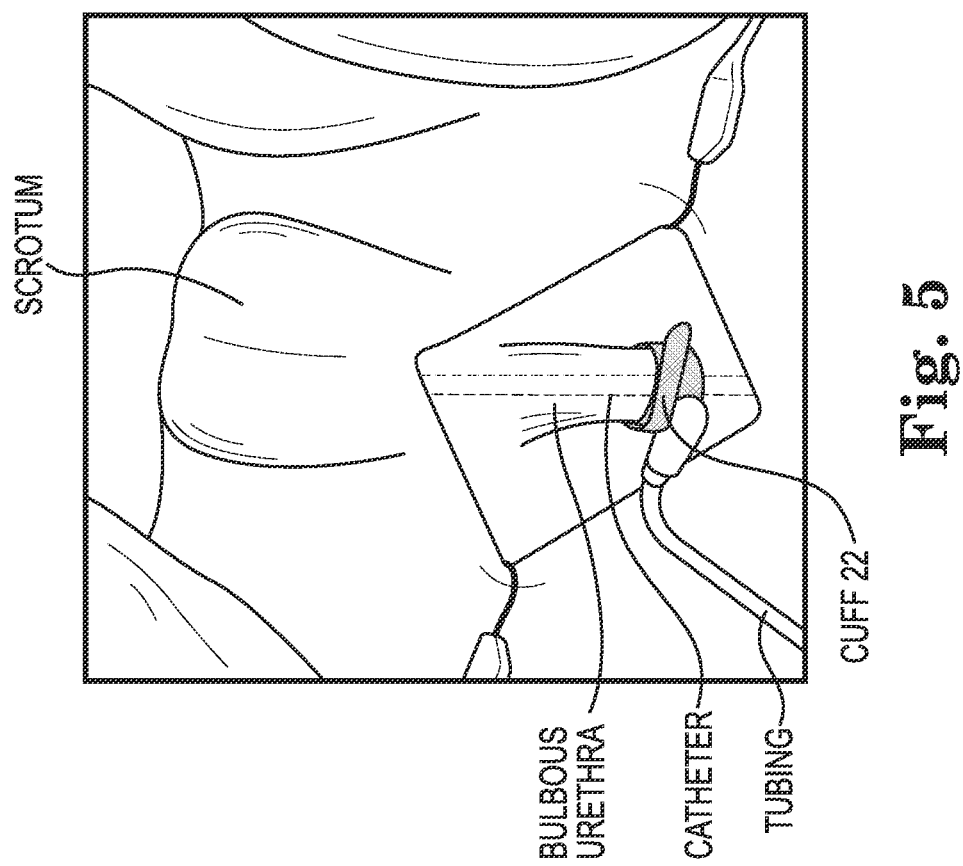
FIG. 5 is a schematic view of a cuff of the urinary control system of FIG. 1 inserted through the single skin incision and placed around the bulbous urethra of the male patient.

FIGS. 3-5 are schematic views of a single perineal skin incision formed to access the bulbous urethra and the retropubic space for placement of the pressure regulating balloon and the pump within the patient.

FIG. 3 is a schematic view of a single (one and only one) incision formed in the skin of a patient.

The male patient is prepped for surgery. The patient is in a lithotomy position with the knees elevated above the head. A catheter is inserted into the urethra to drain urine from the bladder and to provide the urethra with a firmness that can be palpated by the surgeon. The scrotum is elevated cephalad. The surgeon forms a single incision with a scalpel in the perineum between the scrotum and the anus. An angled scissors or other device is employed to dissect tissue and tissue layers away from the inferior side of the bulbar urethra.

FIG. 4 is a schematic view of dissection of tissue to expose the bulbous urethra. Tissue is dissected inferior (i.e., anterior for the patient in in the lithotomy position) to the urethra to expose the front portion of the bulbous urethra. Tissue is dissected laterally relative to the incision as far as the surgeon is able to visualize, leaving tissue connected to the superior (posterior) side of the urethra. The fascia around the bulbospongiosus muscle has been dissected to expose a portion of the bulbar muscle and bulbar urethra for access by the surgeon.

FIG. 5 is a schematic view of the placement of the cuff 22 around the bulbous urethra. The surgeon forms a tissue channel posterior to the bulbous urethra with a tool. The cuff 22 is directed into the tissue channel by guiding a portion of the cuff 22 behind the urethra. The cuff 22 is secured around the urethra. The tubing connected to the cuff 22 is allowed to extend out of the single incision for subsequent attachment to the pump 26.

Figure 6:
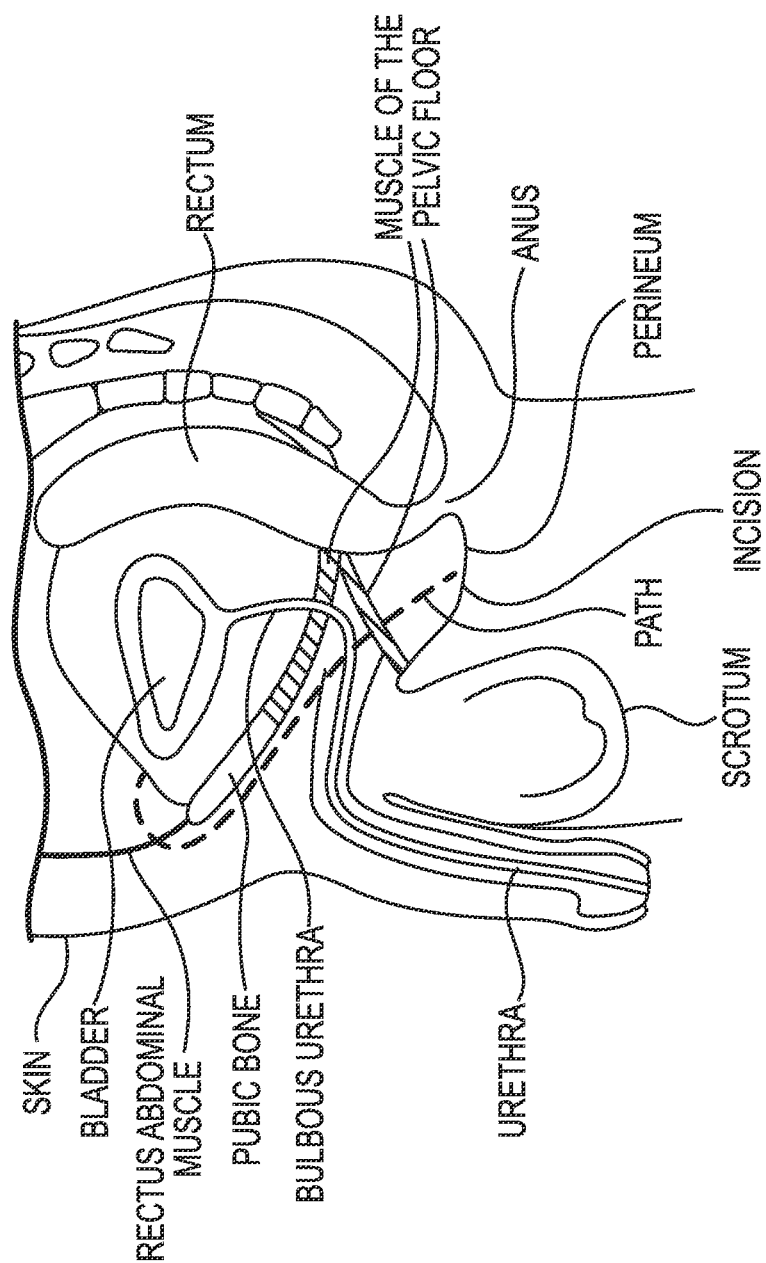
FIG. 6 is a side schematic view of the male pelvic region indicating a pathway for placement of a pressure regulating balloon of the urinary control system of FIG. 1.

FIG. 6 is a side schematic view of the male pelvic region. The perineum is that skin located between the anus and the scrotum. The incision (FIG. 3) has been formed in the perineum and the bulbous urethra is immediately superior to the perineum and superior to the muscles of the pelvic floor. The desired path for placement of the pressure regulating balloon 24 is illustrated extending from the perineal incision, through the muscle of the pelvic floor and anterior to the pubic bone, ending at a location that is superior relative to the pubic bone. In one embodiment, the pressure regulating balloon 24 (or reservoir 24) is passed through the one and only one perineal incision formed in the skin of the patient, through the pelvic floor muscle, directed along the indicated path and placed in a location superior relative to the pubic bone. The surgeon may desire to further locate the pressure regulating balloon 24 posterior to the pelvis in a retropubic space of the patient.

Figure 7:
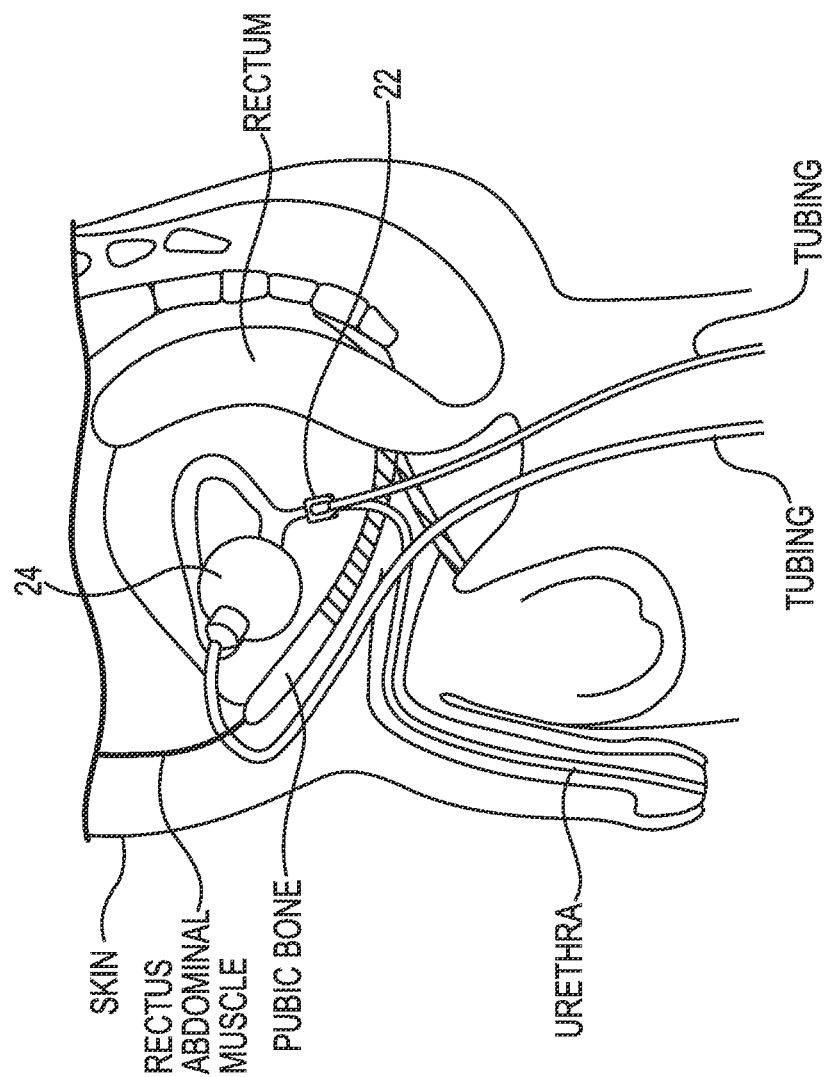
FIG. 7 is a side schematic view of the male pelvic region with the pressure regulating balloon inserted through the single skin incision to a retropubic space of the male patient.

FIG. 7 is a side schematic view of the pelvic region illustrating the pressure regulating balloon 24 implanted in the retropubic space. The pressure regulating balloon 24 has been inserted from the perineal incision through the muscles of the pelvic floor anterior the pubic bone, over the pubic bone and located behind the pubic bone in the retropubic space. The path (FIG. 6) for placement of the pressure relating balloon 24 is anterior to the pubic bone, and thus in the fatty tissue between the rectus abdominal muscle and the skin of the abdomen. The surgeon will guide a tool along the pathway from the perineal incision through the muscles of the pelvic floor to a location superior to the pubic bone and form an opening in the rectus abdominal muscle that is sized to allow the passage of the pressure regulating balloon 24. This approach obviates forming a second incision through the skin. In one embodiment, the tool includes a sharpened distal end to assist in tunnel through the fatty tissue and subsequently puncturing the rectus abdominal muscle to finalize placement of the pressure relating balloon 24. In one embodiment, the tool protects and carries the pressure relating balloon 24 as the tool tunnels through the tissue. The tubing connected to the reservoir 24 is located over the pubic bone and descends along the path (FIG. 6) and out of the perineal incision.

The method of placement of the pressure regulating balloon 24 includes directing the pressure regulating balloon 24 through the inguinal ring along a passage through the inguinal canal. In this alternative and acceptable approach, the pressure regulating balloon 24 (or reservoir 24) is passed through the one and only one perineal incision formed in the skin of the patient, through the pelvic floor muscle, directed along the indicated path and inserted through the inguinal ring to a location in the retropubic space of the patient. The surgeon will generally use a finger to palpate the inguinal ring and begin the movement of the pressure regulating balloon 24 into the inguinal canal. The surgeon may employ a tool to further direct the pressure regulating balloon 24 along and through the inguinal ring until the balloon 24 is in the desired space within the pelvis. Some surgeons refer to this space as the space of Retzius.

Figure 8:
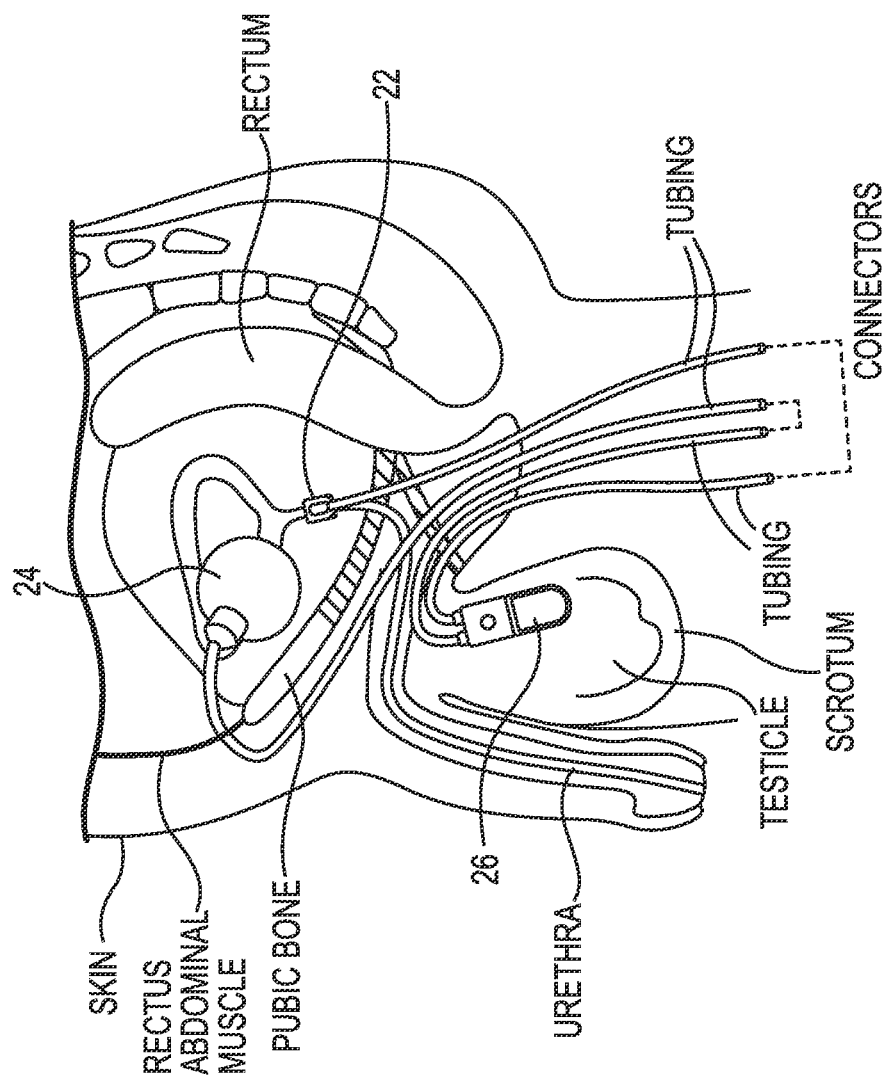
FIG. 8 is a side view of the male pelvic region with a pump of the urinary control system of FIG. 1 inserted through the single skin incision and into a scrotum of the male patient.

FIG. 8 is a side schematic view of the pump 26 implanted in the scrotum. It is sometimes the case that the patient also has had an inflatable penile prosthetic implanted that might include a separate pump located in the scrotum, for example between the testicles. For this reason, in one embodiment the pump 26 is located in the scrotum superior to the testicles, i.e., between the testicles and the penis. In one approach, the surgeon inserts a finger into the single skin incision and into the scrotum to form a pocket in one side of the scrotum. The pump 26 of the urinary control system is placed in the pocket formed in the scrotum.

Figure 9:
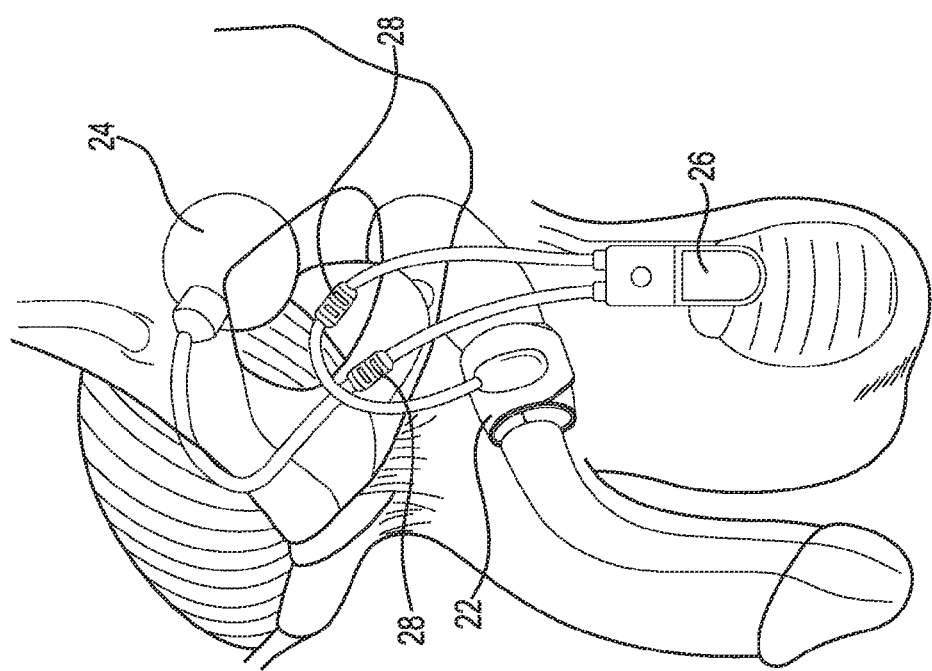
FIG. 9 is a schematic view of the components of the urinary control system of FIG. 1 connected and implanted in the male patient.

FIG. 9 is a side schematic view illustrating the cuff 22 implanted around the bulbous urethra, the pressure regulating balloon 24 implanted within the pelvic region, and the pump 26 implanted in the scrotum. The tubing is measured, cut to the appropriate size, and connected. A connector 28 is used to attach the tubing between the cuff 22 and the pump 26. A separate second connector 28 is used to attach the pressure relating balloon 24 to the pump 26.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A method of implanting a urinary control system in a patient, the method comprising:
    forming one and only one incision in skin of the patient;
    dissecting pelvic floor muscle through the one and only one incision and exposing a bulbous urethra of the patient;
    passing a cuff of the urinary control system through the one and only one incision and through the pelvic floor muscle and securing the cuff around the bulbous urethra of the patient;
    passing a tool through the one and only one incision and through the pelvic floor muscle;
    forming an opening through a rectus abdominal muscle with the tool;
    passing a reservoir of the urinary control system through the one and only one incision and through the pelvic floor muscle and anterior relative to a pubic bone of the patient and through the opening formed in the rectus abdominal muscle and placing the reservoir superior relative to the pubic bone of the patient;
    inserting a pump of the urinary control system through the one and only one incision and into a scrotum of the patient; and
    connecting the cuff to the pump and connecting the reservoir to the pump.

2. The method of claim 1, comprising forming one and only one incision in perineal skin of the patient between the scrotum and anus.

3. The method of claim 1, comprising inserting the pump of the urinary control system through the one and only one incision and through the pelvic floor muscle and locating the pump superior relative to testicles of the patient.

4. A method of treating urinary incontinence, the method comprising:
    forming a single skin incision in a patient and implanting a urinary control system in the patient through the single skin incision, where the implanting includes:
    dissecting pelvic floor muscle through the single skin incision and exposing a bulbous urethra of the patient;
    securing a cuff of the urinary control system around the bulbous urethra of the patient;
    passing a reservoir of the urinary control system through the single skin incision and through the pelvic floor muscle and locating the reservoir in a retropubic space relative to a pubic bone of the patient;
    inserting a pump of the urinary control system through the single skin incision and into a scrotum of the patient and locating the pump between testicles and a penis of the patient;
    connecting the cuff to the pump and connecting the reservoir to the pump; and
    closing the single skin incision.

5. The method of claim 4, comprising forming the single skin incision in perineal skin of the patient.

6. The method of claim 4, comprising passing the reservoir of the urinary control system through the pelvic floor muscle along a path anterior to the pubic bone of the patient.

7. The method of claim 4, comprising parting tissue with a finger and forming a pocket in the scrotum and inserting the pump of the urinary control system into the pocket.

* * * * *